United States Patent [19]

Tsang et al.

[11] 4,221,727

[45] Sep. 9, 1980

[54] ETHYLENE OXIDE RECOVERY

[75] Inventors: Albert C. Tsang; Oliver C. Ainsworth, both of Baton Rouge, La.

[73] Assignee: The Dow Chemical Company, Midland, Mich.

[21] Appl. No.: 67,580

[22] Filed: Aug. 17, 1979

[51] Int. Cl.$^2$ ............................................. C07D 301/32
[52] U.S. Cl. ............................ 260/348.37; 260/348.34
[58] Field of Search ........................ 260/348.37, 348.34

[56] References Cited

U.S. PATENT DOCUMENTS

| 2,437,930 | 3/1948 | Bergsteinsson | 260/348.37 |
| 2,622,088 | 12/1952 | Thomas | 260/348.37 |
| 3,644,432 | 2/1972 | Hoch et al. | 260/348.37 |

FOREIGN PATENT DOCUMENTS

| 44-3806 | 2/1969 | Japan | 260/348.37 |
| 49-25244 | 6/1974 | Japan | 260/348.37 |

*Primary Examiner*—Norma S. Milestone
*Attorney, Agent, or Firm*—A. C. Ancona

[57] ABSTRACT

In the manufacture of ethylene oxide by the partial oxidation of ethylene in the vapor phase, the effluent gases from the reaction are absorbed in water prior to separation and purification of the ethylene oxide. The present invention is the improvement in which ethylene carbonate is employed as the absorbing medium for the ethylene oxide.

9 Claims, 1 Drawing Figure

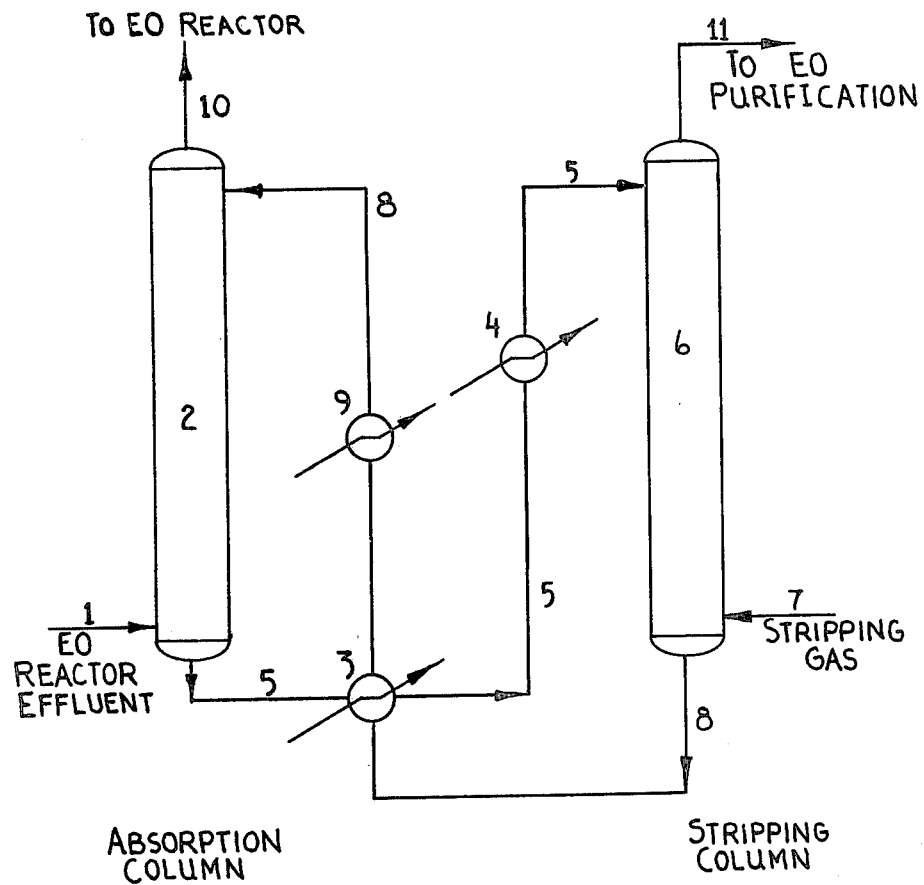

ETHYLENE OXIDE RECOVERY

BACKGROUND OF THE INVENTION

The process of manufacturing ethylene oxide (EO) by oxidation of ethylene with oxygen in the vapor phase produces a product stream which is very dilute in ethylene oxide—on the order of one to two percent. The ethylene oxide is normally recovered by absorbing in water and employs a large counter-current tower for the purpose. Carbon dioxide, which is a by-product, is also absorbed from the product stream, but not as completely as the EO. The water containing the absorbed EO is then passed to a stripping column where the EO is recovered and the water recycled to the absorbing tower.

The absorption process is energy intensive, i.e., the absorbing water must be maintained at about 35° C. in order to accommodate the heat load from the reactor gases and efficiently absorb the EO. Further, the temperature required to desorb the EO from the aqueous solution is about 95° C. At this temperature some of the water evaporates which is a further waste of energy.

It would be highly desirable if an absorption system could be devised which would be less energy intensive and employ smaller apparatus and equipment. Thus, it has now been found that this can be accomplished by employing ethylene carbonate as the absorption medium.

SUMMARY OF THE INVENTION

In the production of ethylene oxide by reacting ethylene with oxygen, or an oxygen-containing gas, over a silver catalyst in the vapor phase, the effluent product gases are absorbed in a liquid, usually water. The improvement of the present invention is in the use of ethylene carbonate in place of water as the absorbing medium which permits a more efficient process and smaller absorption equipment to be used. The present process also provides a feed to an ethylene carbonate process which requires less make-up carbon dioxide.

DETAILED DESCRIPTION OF THE INVENTION

The gas stream containing the ethylene oxide also contains carbon dioxide, oxygen, water, and unreacted ethylene. Ethylene carbonate has a greater affinity for EO and absorbs efficiently at a higher temperature than does water, thus making it unnecessary to cool the absorbing medium to as low a temperature to accommodate the heat of reaction present in the effluent gases. Thus, the operating temperature for absorbing EO in ethylene carbonate is about 45° to 65° C. as contrasted with water at 30° to 40° C. Ethylene carbonate is a better absorbent than water for EO and $CO_2$, i.e., a given volume of absorbent will hold more of the absorbed gases at a given temperature when ethylene carbonate is employed in place of water. Also $CO_2$ is more efficiently absorbed with respect to EO in ethylene carbonate compared to water, i.e., the ratio $CO_2/EO$ absorbed is greater in ethylene carbonate than in water. Thus, $CO_2$ in the recycle gas to the EO reactor will be less. Also the specific heat of ethylene carbonate is about ½ that of water, so the heat applied in the stripping operation to recover the EO will be considerably less.

Since ethylene carbonate and water are miscible in all proportions, water is also absorbed by the ethylene carbonate, but it is readily stripped therefrom by the application of heat and by employing an inert stripping gas.

The composition of the effluent gases from the ethylene oxide process will generally fall within the following ranges of components given as mole percent:

| | |
|---|---|
| $CO_2$ | 0.2–12 |
| $C_2H_4$ | .2–98 |
| $O_2$ | 0.2–7 |
| $H_2O$ | 0.5–3 |
| EO | 0.4–5 |
| $N_2$ | 0. –98 |

The above ranges are broad since the invention is applicable to ethylene oxide processes employing air as the source of oxygen as well as oxygen-enriched air or pure oxygen and also processes employing high ratios of ethylene to oxygen, wherein ethylene makes up a substantial amount of the feed and effluent gases.

Although ethylene, oxygen, and nitrogen are not absorbed to any great extent by ethylene carbonate, the relative amounts of these gases in the effluent affects the actual amount absorbed. Thus, with high ratios of ethylene or in processes using pure oxygen more of these gases will be absorbed.

In a representative operation of the process of the present invention and with reference to the drawing the following detailed description is given:

A reaction product gas which contains 0.05 to 5 volume percent ethylene oxide, (EO) is introduced through line 1 into the lower part of an absorption column 2 which is operated at a pressure in the range of about 165 to about 365 psia. and at a temperature of from about 45° to about 65° C. Ethylene carbonate (EC), containing slight amounts of water and glycol, is introduced through line 8 into the upper part of the absorption column and contacted with the reaction product gas in countercurrent flow, by which the ethylene oxide contained in the reaction product gas is dissolved in the ethylene carbonate absorbent. The liquid removed from the bottom of the absorption column, which contains dissolved ethylene oxide, is sent, via line 5 through cross-exchangers 3 and 4, where it is heated to a temperature within the range of about 90° to about 150° C., thence to the top of stripping column 6 where the ethylene oxide is stripped off by an inert stripping gas, that is inert to EO and EC, e.g., nitrogen or $CO_2$, introduced through line 7 at the bottom of column 6 which is maintained at an operating pressure within the range of about 2 psia. to about atmospheric.

The ethylene carbonate solution, obtained by stripping off the ethylene oxide, is taken off the bottom of column 6 through line 8 to heat exchangers 3 and 9 to cool it before recycling to the absorption column 2.

The gas emerging from the top of the absorption column 2 is returned as recycle gas to the reactor (not shown) through line 10. The vapor containing ethylene oxide, which leaves the upper part of the ethylene oxide stripping column 6 is led through line 11 to the ethylene oxide purification system (not shown).

The pressure of the gas in the absorbing column is substantially that at which the EO reactor is run and is determined thereby.

The liquid/vapor (mole) ratios for the absorbing system are operable from about 0.2 to about 1.0 and are preferably from about 0.35 to about 0.70. For the desorption or stripping system the L/V ratios operates at from about 10–150 with the preferred range being from about 50 to about 125.

Specific details of the operation of the absorbing and the stripping columns are given in Examples 1-4 following:

EXAMPLES 1-3 (Absorption)

An effluent gas stream from an ethylene oxide reactor, containing ethylene oxide, carbon dioxide, small amounts of ethylene, oxygen and water with the remainder being nitrogen, was passed through a column containing ethylene carbonate as the absorbent. Some of the carbon dioxide, but little or no ethylene, nitrogen, and oxygen were absorbed. The ethylene oxide and water were substantially completely absorbed. Table I shows the conditions of temperature pressure and the liquid/vapor ratio (mole) together with the percentage of EO and $CO_2$ removed from the thus treated gas stream.

TABLE I

| Example No. | Temp (°C.) | Press. (psia) | L/V (mole) | Vol. % in Effluent | | Percent Absorbed | |
|---|---|---|---|---|---|---|---|
| | | | | EO | $CO_2$ | EO | $CO_2$ |
| 1 | 50 | 225 | 0.45 | 1.03 | 9.26 | 99.6 | 5.3 |
| 2 | 50 | 225 | 0.37 | 0.99 | 9.08 | 97.9 | 4.5 |
| 3 | 50 | 259 | 1.6 | 0.66 | 8.94 | 98.5 | 2.8 |

EXAMPLES 4 AND 5 (Stripping)

Ethylene carbonate, which had been employed to absorb EO and $CO_2$ from the effluent of an ethylene oxide reactor, was passed to a stripping column where it was heated and contacted with an inert stripping gas (nitrogen). Table II shows the conditions, amounts of absorbed gases, and the percentages of EO and water removed.

TABLE II

| Example No. | Wt.% Absorbate | | Temp. (°C.) | Press (psia) | L/V (mole) | Wt.% Removed | |
|---|---|---|---|---|---|---|---|
| | EO | $H_2O$ | | | | EO | $H_2O$ |
| 4 | 1.0 | 1.0 | 97 | 12 | 61 | 95 | 24 |
| 5 | 0.83 | 1.1 | 95 | 10 | 108 | 93 | 25.5 |

Substantially all of the $CO_2$ absorbed by the ethylene carbonate was removed by the stripping process. Only a few parts per million remain.

We claim:

1. In the process for the manufacture of ethylene oxide wherein ethylene is partially oxidized in the vapor phase with molecular oxygen and wherein the effluent gases from the process are contacted with a liquid absorbent to remove the ethylene oxide product, the improvement which comprises employing ethylene carbonate as the liquid absorbent for the effluent gases from the process in order to more efficiently absorb the ethylene oxide and concurrently absorb a larger quantity of carbon dioxide.

2. The process of claim 1 wherein the liquid absorbent is maintained at a temperature within the range of from about 45° C. to about 65° C.

3. The process of claim 1 wherein the ethylene oxide is separated from the absorbent with an inert stripping gas at a temperature within the range of from about 90° to about 150° C.

4. The process of claim 3 wherein the inert stripping gas is nitrogen.

5. The process of claim 3 wherein the inert stripping gas is carbon dioxide.

6. The process of claim 1 wherein the absorption is conducted under a pressure within a range of from about 165 to about 365 psia.

7. The process of claim 3 wherein the separation of ethylene oxide is accomplished at a pressure within a range of from about 2 to about 15 psia.

8. The process of claim 2 wherein the liquid to vapor (mole) ratio is from about 0.2 to about 1.0.

9. The process of claim 3 wherein the liquid to vapor (mole) ratio is from about 10 to about 150.

* * * * *